United States Patent [19]

Shizuya

[11] Patent Number: 4,472,572

[45] Date of Patent: Sep. 18, 1984

[54] ADENOSINE PYROPHOSPHATE POLYNUCLEOTIDE COMPOUND

[75] Inventor: Hiroaki Shizuya, South Pasadena, Calif.

[73] Assignee: Innovax Laboratories, Ltd., Beverly Hills, Calif.

[21] Appl. No.: 344,790

[22] Filed: Feb. 1, 1982

[51] Int. Cl.³ .................. C07H 19/10; C07H 19/20; C12P 19/34

[52] U.S. Cl. ...................... 536/27; 536/28; 536/29; 435/91

[58] Field of Search .................. 536/27, 28, 29

[56] References Cited

U.S. PATENT DOCUMENTS 4,328,336  5/1982  Robins et al. .................. 536/27

FOREIGN PATENT DOCUMENTS 2071360  3/1972  France ........................ 536/27

OTHER PUBLICATIONS

Smith et al., Cyclic Phosphate. IV. Ribonucleaside-3',5' Cyclic Phosphates, A General Method of Synthesis and some Properties, *The Journal of American Chemical Society,* 8,3 pp. 698–706 (1961).

*Primary Examiner*—Johnnie R. Brown
*Assistant Examiner*—Elli Peselev
*Attorney, Agent, or Firm*—Blakely, Sokoloff, Taylor & Zafman

[57] ABSTRACT

Composition and methods of production of the compound $P^1$-adenosine, $P^2$-(3' nucleotide monophosphate)-5' pyrophosphate (AppNp) are disclosed. AppNp is useful in the synthesis of a predetermined sequence of RNA using the enzyme T4 RNA ligase. The use of this invention in the field of recombinant DNA will greatly enhance the ability to synthesize genes of known composition.

1 Claim, 1 Drawing Figure

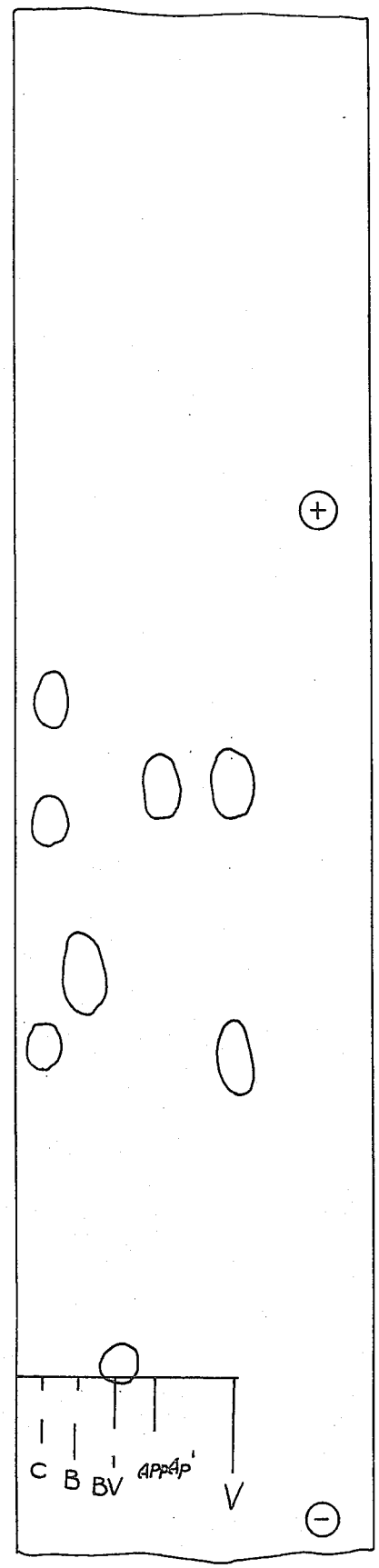

ADENOSINE PYROPHOSPHATE POLYNUCLEOTIDE COMPOUND

BACKGROUND AND PRIOR ART

There are three general steps involved in the production of a protein utilizing genetic engineering techniques. The first step includes laboratory production of or isolation and purification of the desired gene which codes for a particular protein. The second step is the recombination of the gene with a proper transfer vector such as a plasmid. The third step includes transferring the recombined vector into a particular microorganism and inducing the microorganism to produce the particular gene product.

The present invention is directed towards a method of accomplishing the first step. Current methodology for in vitro production of genes by sequential addition of nucleotides consists of using chemical techniques (Itakura, K. and Riggs, A., Science 209:1401 (1980), (Khorana, H. G., Science 203:614 (1979), enzymatic procedures (S. Gillam, P. Jahnke, C. Astell, S. Phillips, C. A. Hutchinson, M. Smith, Nucleic Acids Res. 6,2973 (1979) and solid phase techniques to produce the desired DNA or RNA molecules. The chemical procedures of DNA synthesis are tedious because the reactions involved are non-specific such that extensive purification of the desired product is necessary after each operative step. Thus, synthesis of RNA and DNA by chemical techniques is significantly less desirable than enzymatic systems because greater amounts of starting material are required to produce comparable yields thereby increasing costs, the purification techniques are both time consuming and wasteful where some product is lost at each step, and the large number of steps involved in blocking and unblocking reactive sites provide many opportunities for error and risk of contamination by degradative enzymes which destroy the synthesized product.

Enzymatic synthesis of RNA using polynucleotide phosphorylase and T4 RNA ligase have been reported. The polynucleotide phosphorylase method is limited to production of oligodeoxynucleotides. Under controlled conditions, polynucleotide phosphorylase adds predominantly a single nucleotide to a short oligodeoxynucleotide which is then isolated by chromatographic techniques solid phase techniques are performed by binding the nucleotide chain to a solid support material and using the above chemical methodology to add nucleotides stepwise.

The present invention teaches the composition and method of production of a compound useful in the process of synthesizing a predetermined sequence of RNA using the enzyme T4 RNA ligase. Processes for transcribing the synthesized RNA into DNA so that the synthesized gene may be incorporated into a plasmid, inserted into a microorganism and expressed are known in the art.

The existence, purification and mechanism of the enzyme T4 RNA ligase which is isolated from *Escherichia coli* infected with bacteriophage T4 have been described (Silber, R., Malathi, V. G. & Hurwitz, J., Proc. Natl. Acad. Sci. (1972) 69:3009). This enzyme catalyzes the formation of a phosphodiester bond between the phosphate group on the 5' end of the donor nucleotide and the hydroxyl group on the 3' end of the recipient oligonucleotide as shown below.

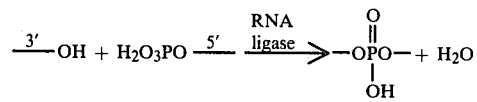

Japanese Patent Application No. 1980-19003 (published Feb. 9, 1980 teaches the utilization of T4 RNA ligase to extend a polynucleotide by adding a single mononucleoside diphosphates (pNp) onto the 3'end of a nucleotide sequence with no terminal phosphate groups. This methodology requires as the starting substrate a trinucleotide, which must be either commercially available or synthesized by chemical means, and requires adenosine triphosphate (ATP) as an energy source for the reaction. Additionally, the invention teaches only the addition of a single base and is not capable of producing oligo or polynucleotides for which sequential addition is required.

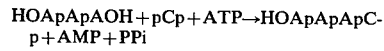

Abbreviations to be used in this application for convenience are provided in Table 1.

TABLE 1

| Abbreviation | Definition |
| --- | --- |
| A(dA) | Adenosine (deoxyadenosine) |
| C(dC) | Cytidine (deoxycytidine) |
| G(dG) | Guanosine (deoxyguanosine) |
| U(dU) | Uridine (deoxyuridine) |
| I(dI) | Inosine (deoxyinosine) |
| T | Thymidine |
| N,X,Y,Z | Any ribonucleotide or deoxyribonucleotide |
| DNA | Deoxyribonucleic acid |
| RNA | Ribonucleic acid |
| BAP | Bacterial Alkaline Phosphatase |
| VPD | Venom phosphodiesterase |
| AppNp | $A^{5'}p^{5'}pN^{3'}p$ (see text for further explanation) |
| >P | 2'-3' cyclized phosphodiester bond |
| ul | Microliter |
| nm | Nanometer |
| TEAB | Triethylammonium Bicarbonate Buffer |
| pA | Adenosine-5'-monophosphate |

The standard form of representing 5' phosphate groups of a nucleotide as preceding the nucleotide abbreviation and the 3' phosphate group as succeeding the nucleotide abbreviation is used herein.

SUMMARY OF THE INVENTION

The present invention teaches the composition and methods of production of the compounds $P^1$-Adenosine, $P^2$-(3' nucleotide monophosphate)-5' pyrophosphate of the form $A^{5'}p^{5'}pN^{3'}p$ (AppNp) where N is any ribonucleotide or deoxyribonucleotide selected from the group Adenosine, Guanosine, Cytosine, Uridine, Thymidine and Inosine. The chemical structure of the ribonucleotide form of the compound is set forth below:

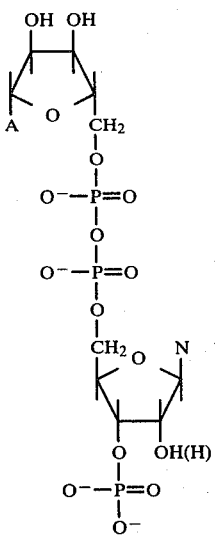

As is disclosed in the copending application Ser. No. 344,789) the reaction of the compound AppNp with an oligonucleotide of the form pXpYOH in the presence of T4 RNA ligase yields an oligonucleotide of the sequence pXpYpNp:

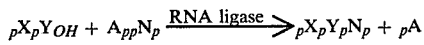

This method for sequentially adding on single nucleotides has the advantage of being fast and specific which means that costs are lower, time of production of a useful product is less and yields are greater with less opportunity for error.

The steps employed to synthesize compounds of the form AppNp are summarized in Table 2. The first step is the conversion of adenosine-5'-monophosphate, which is available commercially to an organic salt. In the second step, a nucleotide-2'(3'), 5' diphosphate (pNp), also available commercially, is converted to a nucleotide-5'-phosphate 2'-3' cyclic phosphate (pN>p) by a procedure described by Khorana, H. G., Tener, G. M., Moffatt, J. G., Pol, E. H. Chem. Ind. (London) 1956 p. 1523. By reacting $A^{5'}p$ with pN>p using chemical means, AppN>p is produced in high yield. Reacting AppN>p with RNase T2 which cleaves the oxygen phosphorous bond produces the desired product AppNp.

TABLE 2

(1) $_pA \xrightarrow{\text{pyridine}} {_p}A$ (pyridinium)

(2) $_pN_p \longrightarrow {_p}N>p$ (3) $_pA + {_p}N>p \longrightarrow A_{pp}N>p$ (4) $A_{pp}N>p \xrightarrow{\text{RNase T2}} A_{pp}N_p$ Similar methods are used to produce AppCp, AppGp, AppUp, AppIp, AppTp, AppdAp, AppdCp, AppdGp and AppdUp. Most of the nucleotide diphosphates necessary for the production of the AppNp compounds are available commercially.

The purity of each of the AppNp compounds may be tested using various enzymatic cleavage experiments which are described in greater detail below and the reaction products from these tests may be identified using electrophoresis and ultraviolet absorption by comparison to known standards.

DESCRIPTION OF THE DRAWING

The drawing is a depiction of a paper electrophoresis pattern under UV light of enzymatic cleavage studies performed on the composition of $P^1$-adenosine, $P^2$-(3' adenosine monophosphate)-5' pyrophosphate (AppAp).

DETAILED DESCRIPTION OF THE INVENTION

This invention teaches a new and useful composition, the chemical compound $P^1$-Adenosine, $P^2$-(3' nucleotide monophosphate)-5' pyrophosphate (AppNp) where nucleotide and N represent any ribonucleotide or deoxyribonucleotide. This invention also teaches methods of production of this family of compounds. The process of this invention will be divided into the following stages:

1. Formation of the pA organic salt;
2. Formation of the pN>p;
3. Chemical bonding of the pA organic salt and the pN>p; and
4. Cleavage of the cyclized phosphate bond.

In order to prepare the pA organic salt, adenosine 5' phosphate which is available in various forms from commercial sources is purified by ion-exchange chromatography or other separation techniques capable of removing impurities. The purified material is then dried, dissolved in pyridine or other organic solvents such as benzene or toluene and the organic salt is formed by addition of tri-n-octylamine or another organic base like tri-n-butylamine. Finally, the pA salt is dried by repeated dissolving and evaporating in anhydrous pyridine.

The nucleotide 5'-phosphate 2'-3' cyclic phosphate (pN>p) is synthesized in the form of a 4-morpholine N, N' dicyclohexylcarboxamidium salt of the nucleotide 2'-3'-cyclic phosphate 5'-phosphoromorpholidate. The piperidate and p-anisidate forms may be used in place of the morpholidate, although lower yields are expected, using techniques described in the prior art. (Moffatt, J. G. and Khorana, H. G., J. Amer. Chem. Soc., 83:649 (1961)).

The next step is to react the pA organic salt with the pN>p salt to form the AppN>p. Each of the reactants is dried separately by repeated dissolving and vacuum evaporation in anhydrous pyridine. The pN>p and pA salts are then combined preferably in a ratio of 1:3, dissolved and evaporated in anhydrous pyridine a few times, and suspended in a small volume of anhydrous pyridine. The reaction material is allowed to incubate at room temperature, although it is anticipated that temperatures of 5°-45° C. would be effective, for 3 to 9 days. Following the incubation, the reaction mixture is dried under vacuum, and resuspended in water and fractionated by column chromatography. To further purify the pooled fraction, the reaction mixture is treated with a phosphatase which removes terminal phosphate groups but not the cyclic phosphate in the N>p position, thereby permitting separation using ion-exchange column chromatography.

The preferred procedure in this laboratory is to fractionate the reaction product on DEAE Sephadex A-25 using a linear gradient of 0.1M to 1.0M TEAB buffer, although it is anticipated that any volatile buffer would be effective. The fourth major peak which contains the AppNp may be concentrated and treated with the phosphatase, preferably BAP F (Worthington Biochemical) under conditions known in the art and fractionated using a DEAE Sephadex A-25 column.

In the final stage, the 2'-3' cyclic phosphodiester bond of the AppN>p is cleaved leaving the find product AppNp by treating the cyclic ribonucleotide with the enzyme which will open the 2'-3' phosphodiester linkage at the 2' position. In the preferred method, RNase T2 is used for all AppNp compounds although RNase T1 may be used for cleavage in the synthesis of AppGp. The reaction conditions for these enzymes are known in the art. To inactivate these enzymes phenol is added to the reaction mixture which is then fractionated on a DEAE Sephadex column. The mixture is applied to the column and the phenol washed off with low ionic strength buffer such as 0.1M TEAB. The reaction product, the AppNp, is then removed with high ionic strength buffer such as 1.0M TEAB.

The reaction product was then tested using various enzymatic cleavage experiments to determine its actual structure.

In all purification steps wherein the above specification provides for fractionation by DEAE Sephadex column chromatography, it is anticipated that the methods such as DEAE chromatography, high pressure liquid chromatography, electrophoresis, gel fitration, thin layer chromatography or any other similar separation techniques may be used without departing from the scope of the present invention.

EXAMPLE

The preferred method for the production of the compound AppNp will now be described.

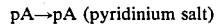
pA→pA (pyridinium salt)

5'-Adenosine monophosphate is converted to the tri-n-octyl ammonium salt by the following method. 200 mg of pA (H+ form obtained from Aldrich) is added to a mixture of approximately 3 ml of H2O:methanol (1:1) and sufficient pyridine is added to dissolve the pA. The solution is then fractionated on a Dowex 50×2 (Dow Chemical) column (0.8 cm² × 10 cm) which has been prewashed with pyridine. Five ul of each fraction was spotted on wet 3 mm paper, rinsed with CCl4 and checked for ultraviolet absorption. Fractions containing ultraviolet absorbable material (pA) were pooled and evaporated to dryness at room temperature. 2 ml of anhydrous pyridine was added with 400 ul of tri-n-octylamine. The material was evaporated to dryness 3 times and then resuspended in 1 ml of anhydrous pyridine.

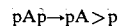
pAp→pA>p

Adenosine 5'-phosphate 2'-b 3' cyclic phosphate (pA>p) is made by the following procedure. 10 mg (0.02 mmole) of 3', 5' adenosine diphosphate (sodium salt) was passed through a column (0.2 cm²×7 cm) of Dowex 50×8 (morpholine form). The column was eluted with water and 1 ml fractions collected. The single peak found was pooled and dried under a vacuum. The residue was dissolved in 190 ul of H2O to which a mixture of morpholine (6.9 ul, 0.2 mmole) in 190 ul of t-butyl alcohol was added. The mixture was heated to reflux. To the refluxing mixture material, a solution of dicyclohexylcarbodiimide (15.7 mg, 0.76 mmole) in 285 ul of t-butyl alcohol was added in 50 ul aliquots over a period of three hours. The reaction was allowed to reflux overnight (or an additional three to twenty-four hours) at 65° to 80° C. The solvents were evaporated under vacuum, and the residue was suspended in 1 ml of H2O. The aqueous solution was filtered to remove any insoluble crystals in a scintered glass filter. The filtrate was evaporated to dryness and the gummy residue dissolved in 50 ul of methanol. 1 ml of ether was added and material shaken vigorously. The resulting milky white solution was then centrifuged for 5 minutes at 1000 xg in a Beckman JA21 rotor (Beckman Instruments) and the clear ether layer decanted. The addition of fresh ether precipitates a gummy solid. 1 ml of ether was added, the sides were scratched and a white powder was formed on the bottom of the tube. The tube was centrifuged and the ether poured off. New ether was added, the sides again scratched and the product, 4-morpholine N,N' dicyclohexylcarboxamidium salt of adenosine 2'3'-cyclic phosphate 5' phosphoromorpholidate, is then air dried.

The reaction product (pA>p) was rendered anhydrous by repeatedly dissolving with anhydrous pyridine and evaporating under vacuum. The tri-n-octyl ammonium salt of adenosine 5'-phosphate (0.06 mmole) was dried in the same manner. The two anhydrous nucleotide salts were combined and twice dissolved and vacuum evaporated with anhydrous pyridine. 400 ul of anhydrous pyridine was used to suspend the material, which was allowed to incubate at room temperature (20° C.). After 6 days, the reaction was dried under vacuum and the residue was dissolved in 1 ml of H2O. A column of DEAE Sephadex A-25 (Pharmacia, 0.2 cm²×25 cm) was equilibrated with 100 ml of 100 mM triethylamine bicarbonate (TEAB) pH 7.6. The sample was applied to the column, washed with 10 ml of 100 mM TEAB and then fractionated by 100 ml of linear gradient of 0.1M to 1.0M TEAB. Fractions of 1 ml were collected and the absorbance measured at 260 nm. The fourth peak containing the reaction product AppA>p was pooled and lyophilized. The lyophilized material was dissolved into 1 ml of H2O to which 460 ul of 1M Tris-HCl pH 8.1 and 75 ul (15 units) of bacterial alkaline phosphatase (BAP F, Worthington) were added and was incubated at 65° C. for 1 hour. The BAP treated mixture was diluted 2 fold, applied to a DEAE Sephadex A-25 column (0.2 cm²×25 cm), washed and eluted as previously described.

To convert the AppA>p to AppAp, the mixture of 250 ul of AppA>p (1.91 mM), 50 ul of 1M potassium acetate (pH 4.8), 20 ul (20 units) RNase T2 [SIGMA, GRADE VI], and 180 ul of H2O was incubated at 37° C. for 1 hour. 500 ul of phenol was added to the reaction mixture and the tube was shaken gently for 10 minutes. The sample was then diluted with 1 ml of 100 mM TEAB pH 7.6, applied to a DEAE Sephadex A-25 column (0.2 cm²×5 cm) and washed with 100 mM TEAB pH 7.6 until the phenol is washed off. The final product is then eluted from the column with 10 ml of 1.0M TEAB pH 7.6. The product AppNp was then treated with various enzymes for characterization.

TESTS

Venom phosphodiesterase (VPD) (Worthington Biochemical) is a exonuclease that cleaves phosphodiester bonds starting from the 3' end of RNA and DNA. Bacterial alkaline phosphatase (BAP) has been described above. Reaction conditions for these enzymes are known in the art. The following reactions were conducted on the final product, which was believed to be the compound AppAp, in order to determine the actual structure of the final product.

In the first reaction, the final product was treated with VPD and then electrophoresed. Two spots were detected under ultraviolet light and identified as Ap and pAp by comparison to known standards.

In the second reaction, the final product was treated with BAP and a single species was detected by ultraviolet light after electrophoresis. The product of this reaction was identified as AppA by comparison to a known standard.

In the third reaction, the final product was treated with BAP and then with VPD which resulted in the formation of a single detectable species, A.

The above-described enzymatic tests are shown in Table 3.

TABLE 3

(1) AppAp $\xrightarrow{VPD}$ Ap + pAp (2) AppAp $\xrightarrow{BAP}$ AppA (3) AppAp $\xrightarrow{BAP}$ AppA $\xrightarrow{VPD}$ 2 pA (if residual BAP) $\longrightarrow$ A Samples of the above reactions were paper electrophoresed in sodium citrate at ph 5.0 for one hour. The results of this test are depicted in the drawing. In column C, a mixture of 3 standards, AMP, ADP, and ATP was spotted. In column V, the VPD treated final product was spotted (Test 1). In column B, the BAP treated final product was spotted (Test 2). Column B/V contains the product of Test (3) above in which the final product was first treated with BAP and then with VPD.

Examining the results of electrophoresis under UV light shows three control spots represent AMP, ADP and ATP in ascending order from the origin. In the B column, only a single species AppA is detected. In the BV column, only a single spot corresponding to A is present. The AppAp column shows the migration of the final product. Finally, the V column shows two spots which correspond to Ap and pAp.

I claim:

1. A compound $P^1$-Adenosine, $P^2$-(3-nucleotide monophosphate)-5' pyrophosphate having the formula:

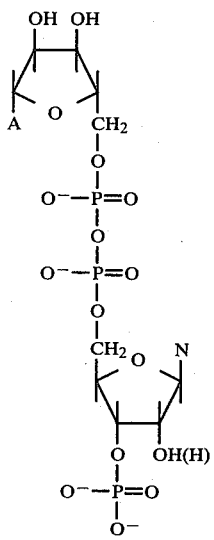

wherein the nucleotide is selected from the group consisting of adenine, guanine, uracil, hypoxanthine, thymidine, deoxyadenine, deoxycytosine, deoxyguanine, deoxyuridine, and deoxyhypoxanthine, whereby said compound may be used to enzymatically add said nucleotide monophosphate specifically to the 3' terminus of an oligonucleotide having a hydroxyl group on said 3' terminus, said addition thereby preventing subsequent continuous additions.

* * * * *